United States Patent [19]

Lawrence

[11] 4,415,754

[45] Nov. 15, 1983

[54] PROCESS FOR PREPARING ANILINE

[75] Inventor: Frederick R. Lawrence, Claymont, Del.

[73] Assignee: E. I. Du Pont de Nemours & Co., Wilmington, Del.

[21] Appl. No.: 458,659

[22] Filed: Jan. 17, 1983

[51] Int. Cl.³ .............................................. C07C 85/11
[52] U.S. Cl. .................................... 564/423; 564/420
[58] Field of Search ................................ 564/420, 423

[56] References Cited

U.S. PATENT DOCUMENTS 1,447,557  3/1923  Legg ............................... 564/420 X
1,854,258  4/1932  Herold et al. ................... 564/420 X
2,560,555  7/1951  Condit ............................ 564/420 X
2,891,094  6/1959  Karkalits et al. .................. 564/420
3,136,818  6/1964  Sperber et al. ..................... 564/420
4,185,036  1/1980  Coosaboon ......................... 564/423

OTHER PUBLICATIONS

Albright et al., "Chem. Eng.", 74, #33, pp. 251–259, 11/67.

Primary Examiner—Paul F. Shaver

[57] ABSTRACT

Aniline can be prepared by catalytic hydrogenation of nitrobenzene containing polynitrophenol impurities. The polynitrophenol impurities are converted to tars, and can be separated and disposed of.

6 Claims, 1 Drawing Figure

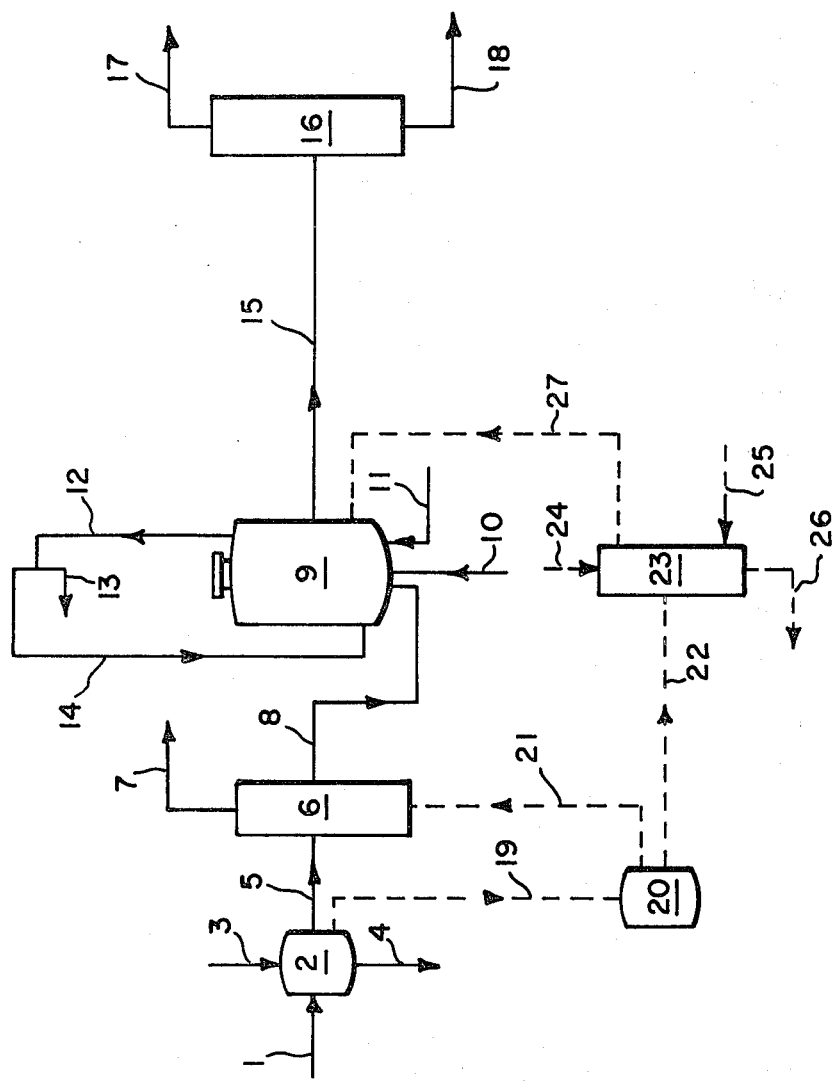

PROCESS FOR PREPARING ANILINE

DESCRIPTION

1. Technical Field

This invention relates to a process for preparing aniline by the hydrogenation of nitrobenzene. It is more particularly directed to a process for preparing aniline by catalytic hydrogenation of acidic nitrobenzene containing polynitrophenol impurities.

BACKGROUND AND SUMMARY OF THE INVENTION

Aniline is a commodity in the chemical industry, widely used in the preparation of dyes, pigments and chemical intermediates. A large proportion of the aniline consumed is produced by hdrogenation of nitrobenzene (NB), which normally contains polynitrophenol (PNP) impurities, chiefly 2,4-dinitrophenol and picric acid. It was heretofore thought desirable that these PNP impurities be removed from the NB before hydrogenation, and this was normally done by extracting them with alkaline water. Although this is a satisfactory method, the PNP impurities are extremely toxic and disposing of them is difficult and expensive.

It has now been found that this extraction of PNP impurities can be dispensed with entirely and that aniline can be prepared by catalytic hydrogenation directly from NB containing these PNP impurities. This converts the PNP impurities to polymeric tars which can be easily separated from the aniline product and disposed of, most preferably by incineration. This is especially advantageous because the NB/aniline reaction itself produces tars, which must be separated from the aniline and disposed of. Thus, when the process of the invention is used, the two types of tar can be separated from the NB product and disposed of together. The costly and time-consuming PNP separation step is thereby eliminated.

BRIEF DESCRIPTION OF THE DRAWING

The drawing is a flow sheet of the process of the invention.

DETAILED DESCRIPTION OF THE INVENTION

The invention can be best described with reference to the drawing.

Crude acidic NB containing about 10-30,000 ppm of PNP impurities, which can be taken directly from a NB preparation facility, is fed via line 1 into vessel 2, where it is washed substantially free of residual mineral acid with water fed into the vessel via line 3. Acidic wash water is removed from the vessel via line 4.

The washed NB is then fed via line 5 into column 6, where liquids with low boiling points are conventionally removed and withdrawn via line 7. The NB, still containing the PNP impurities, is then fed via line 8 into the bottom of sieve-plate reactor 9, where it is continuously and catalytically hydrogenated to aniline at a temperature of 100°-300° C. and a hydrogen pressure of 345-2068 kPa gauge, with a residence time of the reactants in the reactor of 2-30 minutes, and using a conventional liquid phase hydrogenation catalyst, preferably a platinum/palladium/iron-on-carbon support catalyst of the type described in Example X of U.S. Pat. No. 2,823,235 to Graham and Spiegler.

Hydrogen is fed into the reactor via line 10, and a 0.1-3.0% by weight slurry of the catalyst in aniline, preferably recycled from the reactor, is fed in via line 11 at a rate which will continuously provide 0.1-2%, by weight, of catalyst (based on the NB feed) in the reactor (recycle aniline stream is not shown). All of the liquid feeds are heated to 75°-125° C. to initiate reaction.

Water and about 80% by weight of the aniline produced in the reactor are withdrawn in the vapor phase via line 12. This vapor is condensed and the water and aniline separated. The aniline is drawn off via line 13 and the water is recycled to the reactor via line 14 for temperature control. The remainder of the aniline, and the tars (into which the PNP impurities have been converted in the reactor), are withdrawn from the reactor as a liquid via line 15 and passed into column 16, where the aniline and tars are separated by conventional distillation. Aniline is withdrawn from the column via line 17 and the tars are withdrawn via line 18 and disposed of, preferably by incineration.

There is an alternative embodiment of the process of the invention, used when it is desirable to bypass some of the equipment to minimize the corrosive effects of the acidic NB. In this embodiment, NB containing PNP impurities, but from which the mineral acids have been removed, is withdrawn from vessel 2 via line 19 and passed to vessel 20, where the PNP impurities are extracted from the NB and converted to water-soluble salts by mixing about 8 parts of the NB with about 1 part of water and adjusting the pH of the mixture to 9-12 with sodium hydroxide or ammonium hydroxide. The NB phase and the aqueous phase are then separated.

The NB phase is washed with water and passed to column 6 via line 21 and is then processed in the regular fashion. The aqueous extract of water-soluble PNP salts is withdrawn from vessel 20 via line 22 and passed to extractor 23, where the PNP salts are converted back to PNP by bringing the extract to a pH of 0.5-1 with nitric acid or sulfuric acid fed into the extractor via line 24. The PNP is then extracted by and dissolved in NB fed into the extractor via line 25. Spent acid is withdrawn from the reactor via line 26. The PNP/NB solution is washed moderately with water and then fed via line 27 into reactor 9, where the PNP is converted to tar. This tar is withdrawn from the reactor and disposed of as before.

EXAMPLE

In the following example, all parts are by weight.

Crude NB containing 4061 ppm of PNP (130 parts per hour) was continuously fed into vessel 2, where its mineral acid content was reduced to 300 ppm by washing it with water. The NB was then continuously fed via line 19 into vessel 20, where the PNP impurities were converted to water-soluble salts by bringing the pH of the NB to about 10 with aqueous ammonia and then washing with water to remove excess alkalinity. The NB phase was taken from the vessel via line 21 and fed into column 6, where liquids having low boiling points were removed and withdrawn from the column via line 7. The NB (31,149 parts per hour) was then continuously fed via line 8 into reactor 9.

The aqueous phase containing the PNP salts was withdrawn from vessel 20 via line 22 and fed into extractor 23, where the PNP salts were converted to PNP by bringing the aqueous phase to about pH 1 with nitric acid. PNP was then extracted from the aqueous phase with NB, using 1 part NB to 10 parts of water. The resulting 14% PNP in NB solution (714 parts per hour) was washed with water to remove excess acidity and continuously fed to reactor 9 via line 27.

Simultaneously there were fed into reactor 9 the following:
Recycle water (34,264 parts per hour) via line 14
Hydrogen (2346 parts per hour) via line 10
Catalyst slurry (15,468 parts per hour) via line 11.

Slurry is a 1.24% slurry of the catalyst described in Example X of U.S. Pat. No. 2,823,235 in aniline.

All liquid feed streams were heated to 75°–125° C. to initiate reaction. The reactor temperature across the column was held at 120°–230° C. by manipulating the water and catalyst feed rates. Hydrogen pressure was held at about 1723 kPa gauge (250 psig).

A stream of steam and aniline was withdrawn from the reactor via line 12, condensed and the water and aniline separated. The aniline (29,228 parts per hour) was taken off via line 13 and water (34,264 parts per hour) was recycled to the reactor via line 14.

Liquid aniline (2282 parts per hour) was taken from the reactor via line 15 and fed to column 16, where tars and aniline were separated by distillation. Aniline product (2114 parts per hour) was withdrawn from the column via line 17. Tars were withdrawn via line 18 and incinerated.

The aniline product contained less than 5 ppm of PNP. Conversion of PNP to tar was more than 99%, and aniline yield was more than 99%.

I claim:

1. A method for preparing aniline directly from acidic nitrobenzene containing about 10–30,000 ppm of polynitrophenol impurities, the method comprising
    (a) removing substantially all the mineral acid from the nitrobenzene,
    (b) catalytically hydrogenating the nitrobenzene resulting from step (a) to give aniline and tars, and then
    (c) separating the aniline and the tars.
2. The method of claim 1 in which the catalyst used is a platinum/palladium/iron catalyst.
3. The process of claim 1 in which step (b) is performed at 100°–300° C. and a hydrogen pressure of 345–2068 kPa gauge.
4. The process of claim 1 in which step (c) is performed by fractional distillation.
5. The process of claim 1 in which step (a) is performed by extraction with water.
6. The process of claim 1 having, between steps (a) and (b), the additional steps of
    (c) separating the polynitrophenol impurities from the nitrobenzene and converting them into water-soluble salts;
    (d) converting the water-soluble salts back to their original form and dissolving the resulting material in nitrobenzene; and
    (e) feeding the nitrobenzene from (c) and the nitrobenzene solution from (d) separately into step (b) of claim 1.

* * * * *